US012653923B2

(12) United States Patent
Bradford et al.

(10) Patent No.: US 12,653,923 B2
(45) Date of Patent: Jun. 16, 2026

(54) ANTIMICROBIAL FIBRES

(71) Applicant: Advanced Medical Solutions Limited, Winsford (GB)

(72) Inventors: Colin Raymond Bradford, Keighley (GB); Michael David Perkins, Macclesfield (GB); Benjamin Alexander Harrison, Sandbach (GB); Wayne Lee Bonnefin, Chester (GB); Ander Bugedo Albizuri, Chester (GB)

(73) Assignee: Advanced Medical Solutions Limited, Winsford (GB)

( * ) Notice: Subject to any disclaimer, the term of this patent is extended or adjusted under 35 U.S.C. 154(b) by 755 days.

(21) Appl. No.: 17/791,249

(22) PCT Filed: Jan. 7, 2021

(86) PCT No.: PCT/GB2021/050037
§ 371 (c)(1),
(2) Date: Jul. 7, 2022

(87) PCT Pub. No.: WO2021/140331
PCT Pub. Date: Jul. 15, 2021

(65) Prior Publication Data
US 2023/0050073 A1 Feb. 16, 2023

(30) Foreign Application Priority Data
Jan. 8, 2020 (GB) ...................................... 2000250

(51) Int. Cl.
A61L 15/28 (2006.01)
A61L 15/44 (2006.01)

(52) U.S. Cl.
CPC .............. *A61L 15/28* (2013.01); *A61L 15/44* (2013.01); *A61L 2300/206* (2013.01); *A61L 2300/404* (2013.01)

(58) Field of Classification Search
CPC .. A61K 2300/00; A61K 45/06; A61K 31/155; A61K 31/444; A61K 31/785; A61K 31/20; A61K 31/4425; A61K 6/20; A61K 6/30; A61K 6/35; A61K 6/40; A61K 6/54; A61K 6/71; A61K 6/74; A61K 6/76; A61K 6/80; A61K 6/802; A61K 6/84; A61K 6/849; A61K 6/853; A61K 6/86; A61K 6/864; A61K 6/871; A61K 9/0024; A61K 9/0063; A61K 9/143; A61K 9/5115; A61K 31/445; A61K 31/451; A61K 31/522; A61K 47/26; A61K 47/44; A61K 9/0014; A61K 9/0048; A61K 9/107; A61K 9/1075; A61K 31/21; A61K 31/5415; A61K 31/655; A61K 31/7048; A61K 33/06; A61K 38/02; A61K 38/47; A61K 9/0095; A61K 9/08; A61K 9/145; A61K 9/146; A61K 31/4178; A61K 31/422; A61K 31/44; A61K 31/549; A61K 31/5575; A61K 31/56; A61K 31/569; A61K 31/713; A61K 31/728; A61K 36/535; A61K 36/55; A61K 38/179; A61K 47/06; A61K 47/10; A61K 47/14; A61K 47/183; A61K 47/32; A61K 47/36; A61K 47/38; A61K 9/06; A61K 9/7007
See application file for complete search history.

(56) References Cited

U.S. PATENT DOCUMENTS

| | | |
|---|---|---|
| 5,856,248 A | 1/1999 | Weinberg |
| 6,080,420 A | 6/2000 | Qin et al. |
| 6,369,289 B1 | 4/2002 | Orr, III |
| 6,706,279 B1 | 3/2004 | Hazzi |
| 7,704,523 B2 | 4/2010 | Serafica et al. |
| 9,402,770 B2 | 8/2016 | Moghe et al. |
| 9,869,037 B2 | 1/2018 | Agboh |
| 9,907,702 B2 | 3/2018 | Kipke et al. |

(Continued)

FOREIGN PATENT DOCUMENTS

| | | |
|---|---|---|
| CN | 102462860 A | 5/2012 |
| CN | 102580136 A | 7/2012 |

(Continued)

OTHER PUBLICATIONS

JP63021979A abstract translation (Year: 1988).*

(Continued)

*Primary Examiner* — Audrea B Coniglio
(74) *Attorney, Agent, or Firm* — Michael Best & Friedrich LLP

(57) ABSTRACT

Described is a method of manufacturing carboxymethyl cellulose (CMC) fibres containing an antimicrobial, the fibres being suitable for use in the preparation of wound dressings, wherein the antimicrobial is selected from the group consisting of a biguanide, a biguanide derivative, octenidine, taurolidine, and a combination of two or more thereof, the method comprising, submerging CMC fibres comprising at least 95 wt % carboxymethylcellulose on a dry weight basis in a treatment solution for a duration adequate to provide the CMC fibres containing an antimicrobial, the treatment solution comprising the antimicrobial and at least 70 wt % of a water-miscible organic solvent selected from $C_1$-$C_4$ alkanols, $C_3$-$C_5$ ketones, and a combination of two or more thereof. Anti-microbial CMC fibres obtained by the methods and wound dressings containing such fibres are also described.

20 Claims, No Drawings

(56) References Cited

U.S. PATENT DOCUMENTS

| | | |
|---|---|---|
| 10,342,707 B2 | 7/2019 | Wang et al. |
| 2002/0012693 A1 | 1/2002 | Cohen et al. |
| 2002/0064551 A1 | 5/2002 | Edwards et al. |
| 2002/0177828 A1 | 11/2002 | Batich et al. |
| 2003/0049300 A1 | 3/2003 | Terry |
| 2003/0149406 A1 | 8/2003 | Martineau et al. |
| 2003/0203012 A1 | 10/2003 | Serafica et al. |
| 2003/0203991 A1 | 10/2003 | Schottman et al. |
| 2004/0116014 A1 | 6/2004 | Soerens et al. |
| 2004/0116551 A1 | 6/2004 | Terry |
| 2004/0116885 A1 | 6/2004 | Soerens et al. |
| 2004/0142019 A1 | 7/2004 | Serafica et al. |
| 2004/0153040 A1 | 8/2004 | Martineau et al. |
| 2004/0161453 A1 | 8/2004 | Serafica et al. |
| 2005/0214541 A1 | 9/2005 | Berrada et al. |
| 2006/0211972 A1 | 9/2006 | Nielsen et al. |
| 2007/0026056 A1 | 2/2007 | Rolf |
| 2007/0179291 A1 | 8/2007 | Thibodeau et al. |
| 2007/0237812 A1 | 10/2007 | Patel et al. |
| 2008/0206293 A1 | 8/2008 | Toreki et al. |
| 2008/0249206 A1 | 10/2008 | Flohr et al. |
| 2008/0262455 A1 | 10/2008 | Soerens et al. |
| 2008/0312572 A1 | 12/2008 | Riesinger et al. |
| 2009/0022780 A1 | 1/2009 | Scherer et al. |
| 2009/0022801 A1 | 1/2009 | Vachon |
| 2009/0148395 A1 | 6/2009 | Fugmann et al. |
| 2009/0186332 A1 | 7/2009 | Manders et al. |
| 2009/0263469 A1 | 10/2009 | Rohrer et al. |
| 2009/0306157 A1 | 12/2009 | Rohrer et al. |
| 2010/0036334 A1 | 2/2010 | Heagle et al. |
| 2010/0055142 A1 | 3/2010 | Heagle et al. |
| 2010/0055158 A1 | 3/2010 | Vitaris et al. |
| 2010/0055437 A1 | 3/2010 | Fink et al. |
| 2010/0129633 A1 | 5/2010 | Law |
| 2010/0215723 A1 | 8/2010 | Yao |
| 2010/0247544 A1 | 9/2010 | Vachon |
| 2010/0260809 A1 | 10/2010 | Valentova et al. |
| 2010/0262090 A1 | 10/2010 | Riesinger |
| 2011/0104227 A1 | 5/2011 | Andjelic et al. |
| 2011/0171283 A1 | 7/2011 | Riesinger |
| 2011/0213286 A1 | 9/2011 | Riesinger |
| 2011/0238025 A1 | 9/2011 | Law |
| 2011/0256185 A1 | 10/2011 | Yang et al. |
| 2012/0215193 A1 | 8/2012 | Siniaguine et al. |
| 2012/0232502 A1 | 9/2012 | Lowing |
| 2012/0276183 A1 | 11/2012 | Bradford |
| 2012/0310186 A1 | 12/2012 | Moghe et al. |
| 2013/0150764 A1 | 6/2013 | Patel et al. |
| 2013/0171224 A1 | 7/2013 | Percival et al. |
| 2013/0231394 A1 | 9/2013 | Arndt et al. |
| 2014/0044758 A1 | 2/2014 | Wang et al. |
| 2014/0163485 A1 | 6/2014 | Knill et al. |
| 2014/0220842 A1 | 8/2014 | Koltzenburg et al. |
| 2014/0256925 A1 | 9/2014 | Catchmark et al. |
| 2014/0309574 A1 | 10/2014 | Cotton |
| 2015/0010612 A1 | 1/2015 | Vogt et al. |
| 2015/0094672 A1 | 4/2015 | Blucher et al. |
| 2015/0118283 A1 | 4/2015 | Von Blucher et al. |
| 2015/0135644 A1 | 5/2015 | Mo et al. |
| 2015/0157758 A1 | 6/2015 | Blucher et al. |
| 2015/0209187 A1 | 7/2015 | Gutierrez et al. |
| 2015/0283287 A1 | 10/2015 | Agarwal et al. |
| 2015/0335492 A1 | 11/2015 | Tao et al. |
| 2015/0367021 A1 | 12/2015 | Wibaux |
| 2016/0030254 A1 | 2/2016 | Maharaj et al. |
| 2016/0095754 A1 | 4/2016 | Andrews et al. |
| 2016/0095951 A1 | 4/2016 | Locke et al. |
| 2016/0101165 A1 | 4/2016 | Salamone et al. |
| 2016/0101207 A1 | 4/2016 | Parsons et al. |
| 2016/0158403 A1 | 6/2016 | Watson |
| 2016/0270962 A1 | 9/2016 | Wang et al. |
| 2016/0317625 A1 | 11/2016 | Dicosmo |
| 2017/0021050 A1 | 1/2017 | Carlsson et al. |
| 2017/0151314 A1 | 6/2017 | Salamone et al. |
| 2017/0216478 A1 | 8/2017 | Lorenzoni |

| | | | |
|---|---|---|---|
| 2017/0231822 A1 | 8/2017 | Hoggarth et al. | |
| 2017/0239095 A1 | 8/2017 | Hoggarth et al. | |
| 2017/0258956 A1 | 9/2017 | Flach et al. | |
| 2017/0258957 A1 | 9/2017 | Flach et al. | |
| 2017/0367895 A1 | 12/2017 | Holm et al. | |
| 2017/0367896 A1 | 12/2017 | Holm et al. | |
| 2018/0008742 A1 | 1/2018 | Hoggarth et al. | |
| 2018/0014974 A1 | 1/2018 | Hoggarth et al. | |
| 2018/0014975 A1 | 1/2018 | Hoggarth et al. | |
| 2018/0028713 A1 | 2/2018 | Agarwal et al. | |
| 2018/0042980 A1 | 2/2018 | Datt et al. | |
| 2018/0044847 A1 | 2/2018 | Swamy et al. | |
| 2018/0071147 A1 | 3/2018 | Marz et al. | |
| 2018/0094369 A1 | 4/2018 | Koltzenburg et al. | |
| 2018/0207323 A1 | 7/2018 | Chen et al. | |
| 2018/0214596 A1 | 8/2018 | Gupta et al. | |
| 2018/0303674 A1 | 10/2018 | Barrows et al. | |
| 2018/0353637 A1 | 12/2018 | Ko | |
| 2018/0368401 A1 | 12/2018 | Swamy et al. | |
| 2019/0046488 A1 | 2/2019 | Rosenblatt et al. | |
| 2019/0117464 A1 | 4/2019 | Seo et al. | |
| 2019/0133131 A1 | 5/2019 | Percival et al. | |
| 2019/0160197 A1* | 5/2019 | Gardiner | C08G 18/6212 |
| 2019/0282453 A1 | 9/2019 | Hoffmann et al. | |
| 2019/0290676 A1 | 9/2019 | Zhang et al. | |
| 2019/0307904 A1 | 10/2019 | Ballamy | |
| 2019/0351092 A1 | 11/2019 | Silver et al. | |
| 2019/0380880 A1 | 12/2019 | Carlsson | |
| 2020/0016291 A1 | 1/2020 | Wibaux | |
| 2020/0114040 A1 | 4/2020 | Waite et al. | |
| 2020/0129339 A1 | 4/2020 | Drury et al. | |
| 2020/0129648 A1 | 4/2020 | Drury et al. | |
| 2020/0139002 A1 | 5/2020 | Dudnyk et al. | |
| 2020/0179445 A1 | 6/2020 | Buffa et al. | |
| 2020/0188183 A1 | 6/2020 | Hamerslagh et al. | |
| 2020/0188550 A1 | 6/2020 | Dagger et al. | |
| 2020/0197559 A1 | 6/2020 | Bourdillon et al. | |
| 2020/0289701 A1 | 9/2020 | Hall et al. | |
| 2020/0297892 A1 | 9/2020 | Silcock | |
| 2020/0345557 A1 | 11/2020 | Waite et al. | |
| 2020/0345888 A1 | 11/2020 | O'gara et al. | |
| 2020/0375802 A1 | 12/2020 | Metcalf et al. | |
| 2021/0085819 A1 | 3/2021 | Brewster et al. | |
| 2021/0113733 A1 | 4/2021 | Nielsen et al. | |
| 2021/0146000 A1 | 5/2021 | Dagger et al. | |
| 2021/0146002 A1 | 5/2021 | Kharkar et al. | |
| 2021/0169926 A1 | 6/2021 | Abbott et al. | |
| 2021/0170041 A1 | 6/2021 | Luukko et al. | |
| 2021/0244431 A1 | 8/2021 | Hentrich et al. | |
| 2021/0259890 A1 | 8/2021 | Carty et al. | |
| 2021/0290815 A1 | 9/2021 | Parsons et al. | |
| 2021/0346312 A1 | 11/2021 | Hengsberger et al. | |
| 2021/0361820 A1 | 11/2021 | Bourdillon et al. | |
| 2022/0023490 A1 | 1/2022 | Locke et al. | |
| 2022/0118035 A1 | 4/2022 | Buzzi | |
| 2022/0193300 A1 | 6/2022 | Eliyahu-Gross et al. | |
| 2022/0280682 A1 | 9/2022 | Bodkhe et al. | |
| 2022/0347339 A1 | 11/2022 | Derrick et al. | |
| 2024/0050281 A1 | 2/2024 | Leeb et al. | |

FOREIGN PATENT DOCUMENTS

| | | | | |
|---|---|---|---|---|
| CN | 107137749 A | | 9/2017 | |
| DE | 102006001954 | * | 7/2007 | A61L 15/44 |
| DE | 102006001954 A1 | | 7/2007 | |
| EP | 1057481 A1 | | 12/2000 | |
| EP | 1438975 A1 | | 7/2004 | |
| EP | 3061864 A1 | | 8/2016 | |
| EP | 3078360 A1 | | 10/2016 | |
| EP | 3281614 A1 | | 2/2018 | |
| EP | 3434237 A1 | | 1/2019 | |
| FR | 2972355 A3 | | 9/2012 | |
| GB | 821113 A | | 9/1959 | |
| GB | 2401879 A | | 11/2004 | |
| GB | 2489541 A | | 10/2012 | |
| GB | 2531344 A | | 4/2016 | |
| GB | 2531345 A | | 4/2016 | |
| GB | 2537008 A | | 10/2016 | |
| GB | 2537009 A | | 10/2016 | |

(56) References Cited

FOREIGN PATENT DOCUMENTS

| | | | | | |
|---|---|---|---|---|---|
| GB | 2537010 | A | 10/2016 | | |
| GB | 2554651 | A | 4/2018 | | |
| GB | 2489947 | B | 12/2018 | | |
| GB | 2579800 | A | 7/2020 | | |
| JP | 63021979 | A | * 1/1988 | ............ | C11D 3/222 |
| JP | S6321979 | A | 1/1988 | | |
| WO | 0028978 | A1 | 5/2000 | | |
| WO | 03061538 | A1 | 7/2003 | | |
| WO | 0247737 | A1 | 9/2003 | | |
| WO | 03092756 | A1 | 11/2003 | | |
| WO | 2003093357 | A1 | 11/2003 | | |
| WO | 2004062600 | A2 | 7/2004 | | |
| WO | 2005030279 | A1 | 4/2005 | | |
| WO | 2007120616 | A2 | 10/2007 | | |
| WO | 2008122929 | A1 | 10/2008 | | |
| WO | 2009043839 | A1 | 4/2009 | | |
| WO | 2009080218 | A2 | 7/2009 | | |
| WO | 2012062139 | A1 | 5/2012 | | |
| WO | 2012092813 | A1 | 7/2012 | | |
| WO | 2012122956 | A1 | 9/2012 | | |
| WO | 2012160217 | A1 | 11/2012 | | |
| WO | 2012171916 | A1 | 12/2012 | | |
| WO | 2012171920 | A1 | 12/2012 | | |
| WO | 2013113906 | A1 | 8/2013 | | |
| WO | 2013164016 | A1 | 11/2013 | | |
| WO | 2014020133 | A2 | 2/2014 | | |
| WO | 2015173547 | A1 | 11/2015 | | |
| WO | 2016057788 | A1 | 4/2016 | | |
| WO | 2016107856 | A1 | 7/2016 | | |
| WO | 2016108041 | A1 | 7/2016 | | |
| WO | 2016115637 | A1 | 7/2016 | | |
| WO | 2016135038 | A1 | 9/2016 | | |
| WO | 2016206638 | A1 | 12/2016 | | |
| WO | 2017085436 | A1 | 5/2017 | | |
| WO | WO2017085436 | | * 5/2017 | ............ | A61L 15/28 |
| WO | 2017108770 | A1 | 6/2017 | | |
| WO | 2018023021 | A1 | 2/2018 | | |
| WO | 2018078084 | A1 | 5/2018 | | |
| WO | 2018125993 | A1 | 7/2018 | | |
| WO | 2019011000 | A1 | 1/2019 | | |
| WO | 2020261187 | A1 | 12/2020 | | |
| WO | 2021009713 | A1 | 1/2021 | | |
| WO | 2021015631 | A1 | 1/2021 | | |
| WO | 2021240271 | A1 | 12/2021 | | |

OTHER PUBLICATIONS

Halib et al., "Potential Applications of Nanocellulose-Containing Materials in the Biomedical Field", Materials, 2017, 31 pages.

U.S. Appl. No. 62/098,058, filed Dec. 30, 2014 in the name of 3M Innovative Properties Company.

U.S. Appl. No. 62/112,74, filed Feb. 6, 2015 in the name of 3M Innovative Properties Company.

International Preliminary Report on Patentability for Application No. PCT/GB2021/050037 dated Jul. 12, 2022 (6 pages).

United Kingdom Patent Office Search report for Application No. GB2000250.7 dated Jul. 24, 2020 (5 pages).

PRC National Intellectual Property Administration Supplementary Novelty Search Report for Application No. GC2021-41250 dated Apr. 7, 2022 (4 pages).

United Kingdom Patent Office Further Search Report for Application No. GB2000250.7 dated Jan. 28, 2021, Claims Searched:28 and 29 in full and 30-33 and 35-38 in part (2 pages).

United Kingdom Patent Office Further Search Report for Application No. GB2000250.7 dated Jan. 28, 2021, Claims Searched: 34 in full and 35 in part (2 pages).

* cited by examiner

ANTIMICROBIAL FIBRES

RELATED APPLICATIONS

This application is the U.S. national stage entry, under 35 U.S.C. § 371, of International Application Number PCT/GB2021/050037, filed Jan. 7, 2021, which claims priority to Great Britain Application Number 2000250.7, filed Jan. 8, 2020, the entire contents of each of which are hereby incorporated by reference.

FIELD OF THE INVENTION

The present invention relates to a method of manufacturing carboxymethylcellulose (CMC) fibres containing an antimicrobial agent for use in wound dressings, particularly carboxymethylcellulose fibres comprising polyhexamethylene biguanide (PHMB). Anti-microbial CMC fibres obtainable by such methods are described, as are wound dressings containing such fibres. The present invention is particularly relevant to the manufacture of fibrous non-woven components of wound dressings.

BACKGROUND

Wound dressings are widely used to assist in the healing process of wounds. Wounds may vary in severity, from grazes to cuts, to deep wounds caused by trauma or surgery. It is generally desirable that wound dressings are flexible so that the medical practitioner can adapt the wound dressing to be in conformity with the profile of the wound. Moreover, flexibility in the wound dressing allows the patient to move more freely, without causing undesirable damage to the wound and the healing tissue. It is also desirable that wound dressings have a soft feel, to provide comfort for the patient and to reduce damage to the wound and/or pain caused by the dressing.

Some wounds, particularly chronic wounds caused by trauma or surgery, excrete a liquid exudate comprising mainly water along with salts, proteins for assisting in the healing process, as well as cells such as white blood cells. During the healing process, it is desired that the wound be kept moist to help in the healing process, but not too moist as this may increase the risk of infection and impair healing. It is therefore desirable that wound dressings also be absorbent.

Wound dressings comprising gelling fibres are known, owing to their ability to absorb wound exudate whilst maintaining a desirable moist environment for wound healing and a conformable wound contact surface. Upon absorption of water from the wound exudate, the gelling fibres undergo an irreversible gelling process. Wound dressings comprising gelling fibres can promote granulation tissue and assist in healing. The dressing may, for example, be in the form of a non-woven felt. When wound dressings made from gelling fibres are applied to a wound (such application often being in conjunction with a secondary dressing such as a breathable film that overlies the fibrous dressing) exudate from the wound is absorbed by the dressing, which results in the dressing converting it into the form of a gel. Such gels are advantageous in wound care because they maintain an ideal moist wound environment and "lock-in" the wound exudate that has been absorbed. The fibres used for producing the wound dressing generally produce a gel of sufficient integrity so as not to disintegrate within the wound, at least within the time for which the dressing is intended to remain in place, so the dressing may be removed intact from the wound.

Carboxymethylcellulose (CMC) has been commonly employed as a gelling polymer in the preparation of wound dressings due to its desirable physical and chemical properties in the context of wound care applications. CMC fibres for use in wound dressings are conventionally prepared by carboxymethylation of pre-prepared cellulose fibres (cellulose fibres are also known as viscose or rayon). This approach (i.e. carboxymethylation of a pre-prepared fibre) is adopted because CMC in powder form is not capable of forming fibres by conventional processes such as spinning. Thus, it is necessary to pre-prepare fibres (of a fibre-forming material such as cellulose) that can be carboxymethylated. Thus, for example, EP0616650 discloses a process in which solvent-spun cellulose fibre is carboxymethylated by reaction with a solution containing a strong alkali (e.g. sodium hydroxide) and a monochloroacetate reagent (e.g. sodium chloroacetate). The degree of substitution is controlled by the concentration of the components in the reaction solution and the processing conditions.

The inability of CMC powder per se to be fibre-forming is in contrast to coagulating polymers like alginates, which readily form fibres by conventional fibre forming techniques (such as by spinning an aqueous solution ("dope") of a soluble form of the alginate (e.g. the sodium salt) through a spinneret into a coagulation bath containing multi-valent cations (usually calcium) that cross-link the alginate to form fibres).

CMC fibres per se have been used as a wound-contacting surface in wound dressings, as described in WO9416746. Wound dressings have been proposed containing CMC fibres and alginate fibres. For example, EP0783605 describes wound dressings comprising CMC fibres and alginate fibres. Wound dressings have also been disclosed containing fibres comprising CMC co-spun with alginate, to form fibres that each contain a homogenous mixture of CMC and alginate. Processes for co-spinning alginate and CMC to form fibres containing a mixture of both materials are for instance described in WO2017/085436.

It is well known to include anti-microbial agents in wound dressings to reduce infection during use. When anti-microbials are included, it is desirable to achieve a suitable loading in the dressing and for the anti-microbial to be releasable at a suitable rate. In this regard, it is desirable that the dressing elute at least some of anti-microbial to allow the anti-microbial effect to be observed at the site of the wound. Different fibre polymer/anti-microbial combinations will demonstrate different loading/elution properties. The incorporation of anti-microbial agents into a dressing can however have an impact on the processability of the wound dressings/polymer fibres and may, in some cases, lead to less desirable physical properties (e.g. stiffness) relative to wound dressings provided without the anti-microbial agent.

For instance, for some wound dressing polymer materials, anti-microbial agents may be readily incorporated into the fibre polymer during the initial fibre-forming step. This is, for instance, possible in the case of alginate fibres. Alginate fibres for wound dressings are typically prepared by a wet-spinning process whereby a soluble alginate is contacted with a calcium salt to cause crosslinking, thereby causing the fibre polymer to coagulate into fibres, as described above. During such processes, anti-microbial compounds may be either dissolved or suspended in the polymer solution ("dope") to be incorporated into the resulting coagulated fibres in situ.

Such methods are not, however, suitable for CMC fibres, which are not producible by the sort of spinning methods described above for alginates. As already described above, CMC fibres for use in wound dressings are usually prepared by functionalisation (carboxymethylation) of pre-formed cellulose fibres. This is usually by treating the cellulose with a carboxymethylating treatment composition, followed by washing steps, to remove unreacted reagent, by-products, and any excess water. As such, the manufacture of CMC fibres typically based on modification of a pre-existing fibre, not by coagulation of a new fibre as in the case of alginates or similarly coagulatable polymers.

In view of this, it is conventional for anti-microbial agents to be applied to CMC fibres only after formation of the CMC fibres has taken place, which can produce a number of drawbacks, particularly when highly water-soluble anti-microbial agents such as polyhexamethylene biguanide (PHMB) are sought to be used.

PHMB is an anti-microbial agent having particular utility in the field of wound dressings. It is a highly water-soluble compound, and exhibits poor solubility in organic solvents. As such, prior art methods for applying PHMB to CMC wound dressings generally rely on application of an aqueous solution of PHMB following formation of the wound dressing. An example of such a method of applying an aqueous solution of PHMB to a fibrous non-woven CMC wound dressing is described in CN102462860, whereby the pre-formed non-woven wound dressing is sprayed with an aqueous solution of PHMB. This method, however, has a number of drawbacks. Firstly, spraying the final formed wound dressing results in only the outer surface of the fibrous dressing being coated with PHMB. In essence, this means that the distribution of PHMB is highly localised to the wound dressing surface. Whilst this may allow the anti-microbial to contact the wound, it would not prevent microbes from growing within the deeper body of the wound dressing, where such microbes may then potentially re-infect the wound. Moreover, such spraying methods are more prone to the aqueous solution of PHMB being applied in a non-uniform manner, which may result in areas of relatively high PHMB concentration and areas of relatively low PHMB concentration on the wound-dressing surface. Additionally, and importantly, CMC fibres undergo a gelling process upon contact with water. Known methods of applying PHMB to CMC fibres/wound dressings using aqueous solutions are therefore prone to causing premature gelation of the CMC fibres. Once fibres have been caused to gel and then are allowed to dry (even if only having gelled in part), the resulting fibres are more brittle and experience diminished softness/conformability (increased stiffness) compared to CMC fibres provided without the anti-microbial treatment. This change in physical properties is irreversible. These are undesirable properties for a patient and will not only diminish patient comfort (which may therefore decrease patient compliance) but may also lead to reduced conformity to the wound, and a less desirable wound environment for healing.

It is an object of the present invention to mitigate or obviate one or more of the problems identified above.

It is for instance desirable to provide anti-microbial CMC fibres/wound dressings containing such fibres, which retain a desirable conformability and softness; and/or to provide wound dressings containing anti-microbial agent throughout the fibrous wound dressing; and/or which achieve desirable loading of anti-microbial agent into CMC fibres and/or elution from CMC fibres.

SUMMARY OF INVENTION

At its most general, the present invention provides new and advantageous methods of preparing antimicrobial CMC fibres for wound dressing applications, as well as providing resulting anti-microbial CMC fibres and wound dressings comprising such CMC fibres. Advantageously, the present invention obviates issues associated with applying aqueous antimicrobial solutions directly to CMC wound dressings, as is conventional in the art.

The inventors have in particular developed a method whereby water-soluble organic anti-microbial agents such as PHMB can be incorporated into CMC fibres for wound dressings in adequate loadings and whilst applying the anti-microbial evenly to the fibre, but without experiencing the reduction in conformability and softness associated with aqueous treatment methods described in the prior art. In particular, it was surprisingly observed by the inventors that by utilising a treatment solution containing PHMB and at least 70 wt % organic solvent, PHMB was loaded into CMC fibres in adequate quantities but without any observed gelation of the CMC fibre polymer, thus leading to more conformable fibres and dressings.

Moreover, by virtue of the methods proposed herein, CMC fibres are evenly exposed to the anti-microbial agent, allowing for a consistent antimicrobial release profile across the fibre length. The disclosure thus contemplates use of the resulting fibres in the manufacture of fibrous wound dressings, e.g. non-wovens also advantageously produces fibrous articles for wound dressings, or dressings themselves, wherein the antimicrobial agent may be distributed throughout the article/dressing. This has the advantage that the anti-microbial effect may not only be provided at the wound contact surface, but also within the entire body of the dressing to prevent microbes from growing within the dressing, thus reducing the chance of reinfection of the wound. Additionally, because of the convenient nature of the treatment step of the invention, the present methods of the invention can be readily incorporated as a step (e.g. a wash step) in the manufacturing process of CMC fibres, as is evident in embodiments described herein. The present methods also therefore provide versatility and efficiency, obviating the need for applying anti-microbials after manufacture of the wound dressing, such as described in CN102462860, referenced above.

According to a first aspect of the present invention, there is provided a method of manufacturing carboxymethylcellulose (CMC) fibres containing an antimicrobial, the fibres being suitable for use in the preparation of wound dressings, wherein the antimicrobial is selected from the group consisting of a biguanide, a biguanide derivative, octenidine, taurolidine, and a combination of two or more thereof, the method comprising:

submerging CMC fibres comprising at least 95 wt % carboxymethylcellulose by dry weight basis in a treatment solution, the treatment solution comprising:

a) the antimicrobial, optionally in an amount of from 1-10 wt %; and b) at least 70 wt % of a water-miscible organic solvent selected from $C_1$-$C_4$ alkanols, $C_3$-$C_5$ ketones, and a combination of two or more thereof;

for a duration adequate to provide the CMC fibres containing the antimicrobial.

This method advantageously allows water-soluble organic anti-microbial agents such as PHMB to be incorporated into CMC fibres for wound dressings in adequate loadings and whilst applying the anti-microbial evenly to the fibre. This is without experiencing the reduction in conformability and softness associated with aqueous treatment methods described in the prior art. By utilising a treatment solution containing the anti-microbial and at least 70 wt % organic solvent, PHMB was loaded into CMC fibres in adequate quantities but without any observed gelation of the CMC fibre polymer.

Advantageously, in accordance with the present invention, the method is able to produce carboxymethylcellulose (CMC) fibres containing an antimicrobial prior to incorporation of the fibres into an article, e.g. a woven or non-woven article, or dressing containing such article. In typical embodiments, the method does not include submerging fibres other than the CMC fibres comprising at least 95 wt % carboxymethylcellulose by dry weight basis in the treatment solution as described above. In other words, the CMC fibres described may be the sole fibres submerged according to the method.

The treatment solution may comprise from 1-10 wt % of the antimicrobial; and at least 70 wt % of a water-miscible organic solvent relative to the total weight of the treatment solution. The high wt % of organic solvent advantageously prevents the CMC fibres from prematurely gelling but simultaneously allows delivery of the anti-microbial. The present invention therefore advantageously allows an anti-microbial to be delivered to the CMC fibres, whilst avoiding undesirable and irreversible premature gelling of the CMC fibres, which can lead to brittleness and stiffness, as described above.

Without wishing to be bound by theory, it is believed that the solvent in the treatment solution causes swelling of the CMC polymer fibre without gelling, thus allowing the anti-microbial agent in the treatment solution to enter the polymer fibre matrix to provide adequate loading and, in embodiments, an even distribution of anti-microbial within the fibre. Embodiments of CMC fibres prepared in accordance with the present invention are provided with an antimicrobial within the polymer matrix, and advantageously retain desirable conformability. Moreover, as described in more detail below, the method according to the present invention may be readily and conveniently incorporated into the manufacturing process of the CMC fibres, e.g. from starting cellulose, thereby reducing waste solvent and increasing efficiency and productivity.

Antimicrobials, such as biguanides (such as PHMB) and biguanide derivatives, generally have excellent solubility in water, but are typically only sparingly soluble in organic solvents. For example, PHMB is very soluble in water (426 g/L), but has poor solubility in organic solvents ($10^{-3}$ g/L). For example, PHMB only exhibits solubility in ethanol of up to 0.5 wt % at ambient temperature. It has been surprisingly found that submerging CMC fibres in a treatment solution comprising a high organic solvent content and an antimicrobial selected from those claimed, for example PHMB, nonetheless provides desirable final concentrations of anti-microbial in the CMC fibres containing the antimicrobial.

According to a second aspect of the present invention, there is provided a carboxymethylcellulose (CMC) fibre containing an antimicrobial selected from the group consisting of a biguanide, a biguanide derivative, octenidine, taurolidine, and a combination of two or more thereof, for use in the preparation of wound dressings, the CMC fibre being obtained or obtainable by a method according to the first aspect of the present invention.

As described above, such fibres contain adequate loading of anti-microbial agent and advantageously exhibit improved conformability/softness relative to anti-microbial CMC fibres that have been prepared by treatment of CMC fibres with aqueous anti-microbial compositions.

According to a third aspect of the present invention, there is provided a carboxymethylcellulose (CMC) fibre containing an antimicrobial selected from a biguanide, a biguanide derivative, octenidine, taurolidine, and a combination of two or more thereof for use in the preparation of wound dressings, wherein the antimicrobial is dispersed throughout the fibre polymer. Without wishing to be bound by theory, it is believed that the solvent in the treatment solution causes swelling of the CMC polymer fibre, thus allowing the anti-microbial agent in the treatment solution to enter the polymer fibre matrix, which in accordance with this aspect of the invention, provides antimicrobial dispersed throughout the fibre polymer, e.g. evenly dispersed.

According to a fourth aspect of the present invention, there is provided a carboxymethylcellulose (CMC) fibre containing an antimicrobial selected from a biguanide, a biguanide derivative, octenidine, taurolidine, and a combination of two or more thereof for use in the preparation of wound dressings, wherein the CMC fibre polymer has not undergone gelation. As described above, methods of the invention are advantageously able to produce CMC fibres containing anti-microbials whilst avoiding gelling of the CMC, by delivering the anti-microbial in a treatment solution containing high levels of organic solvents (and therefore relatively low levels of water). This is in contrast to methods of the prior art which use aqueous treatment methods to deliver anti-microbials such as PHMB to CMC fibres, thus leading to premature gelling.

According to a fifth aspect of the present invention, there is provided a woven, non-woven or knitted material comprising CMC fibres containing an antimicrobial, wherein the CMC fibres containing an antimicrobial are defined according to any one of the second, third or fourth aspects of the invention. The material is preferably a non-woven and most preferably a felt.

According to a sixth aspect of the present invention, there is provided a non-woven material (preferably a felt) comprising entangled CMC fibres containing an antimicrobial, wherein the antimicrobial is selected from a biguanide, a biguanide derivative, octenidine, taurolidine, and a combination of two or more thereof, wherein the non-woven material exhibits a conformability characterised by an overhang length in the longitudinal direction of up to 6.5 cm, as determined by the Cantilever method described in ASTM D1388-08. This Cantilever method and methods of preparing the non-woven for the Cantilever testing are described in more detail herein in the examples section. Methods described herein advantageously allow production of CMC fibres containing an anti-microbial agent whilst avoiding premature gelation. This therefore ensures that the CMC fibres retain softness, enabling production of resulting wound dressings that contain anti-microbial agent, but which still exhibit desirable conformability, as demonstrated by the relatively low overhang lengths recited, as determined by the Cantilever method.

According to a seventh aspect of the invention, there is provided a wound dressing comprising CMC fibres containing an antimicrobial, wherein the CMC fibres containing an antimicrobial are defined according to any one of the second, third or fourth aspects of the invention. The wound dressing may for instance contain a material according to the fifth or sixth aspects of the invention. The wound dressing may contain the material as the sole layer of the wound dressing, or typically, the wound dressing may be a multi-layer dressing wherein the material is present as a layer within the multi-layer dressing.

The aspects and embodiments of the present invention will now be described in more detail by way of example only.

General Definitions

As referred to herein, "carboxymethyl cellulose (CMC)" refers to cellulose containing pendant carboxymethyl groups bound to some of the hydroxyl groups of the glucose monomers that make up the cellulose backbone. Such carboxymethyl groups may typically be provided by reaction of cellulose starting material (such as rayon, e.g. viscose) with a carboxymethylating agent to cause carboxymethylation of free hydroxyl groups. In embodiments of the invention, the CMC (e.g. of the CMC fibres) is characterised by a degree of substitution of from 0.05 to 0.8, typically 0.65, which is intended to mean that from 0.05 to 0.8 carboxymethyl groups are provided per glucose unit, as determined by potentiometric titration. Carboxymethyl groups will be understood to be a —$CH_2COOH$ group, wherein the carboxymethyl group is bound to the cellulose backbone via a pendant hydroxyl group to form an ether bond i.e. —$OCH_2COOH$.

Unless expressly defined otherwise herein, the term "carboxymethylcellulose (CMC) fibre" is intended to refer to a fibre consisting of, or consisting essentially of, CMC as the structural fibre polymer, e.g. wherein the fibre-forming polymer component is at least 95 wt % CMC, such as 96, 97, 98 or 99 wt % CMC. A CMC fibre according to the present invention will therefore be substantially absent, or in embodiments entirely absent, of structural fibre polymers other than CMC, e.g. wherein the fibre-forming polymer component contains less than 5 wt %. of structural fibre polymers other than CMC, such as less than 4 wt %, 3 wt %, 2 wt % or 1 wt % of structural fibre polymers other than CMC. Examples of structural fibre polymers include those typically used for forming fibres in wound dressings and include alginates. Other examples will be readily apparent to the skilled person. Preferably, the CMC fibres are absent of alginate. It will however be appreciated that minor amounts of undesired polymeric impurities, or other intended polymeric materials that do not form the structural fibre matrix itself (e.g. surfactants, spin finish agents, or other wound care additives) may be present, and such components are not intended to be excluded by the term "CMC fibres" (e.g. wherein such additives may be encompassed by or otherwise contained within the fibre matrix, but are not part of the structural matrix itself). Embodiments of CMC fibres according to the invention may thus contain such additives, which may for instance include surfactants and/or spin finish agents. Examples of spin finish agents are surfactants. A preferred example is polysorbate, e.g. polysorbate 20 (Tween).

Within the context of the present invention, the term "biguanide" refers to the class of anti-microbial compounds containing a biguanide moiety, including biguanides that contain pendant substituents such as one or more $C_1$-$C_8$ alkyl groups, $C_1$-$C_8$ alkoxy groups, and/or an aryl-$C_{1-8}$alkyl group, e.g. phenylethyl group. Such compounds may contain multiple biguanide moieties and may for instance include biguanide polymers.

Well-known examples of biguanides include polyaminopropyl biguanide (PAPB), polyhexamethylene biguanide (PHMB), metmorfin (dimethylbiguanide), phenformin (phenethylbiguanide), propylbiguanide, buformin (butylbiguanide), hexylbiguanide, alexidine and chlorhexidine, with PHMB being particularly preferred.

Herein, the terms "antimicrobial", and "antimicrobial agent" are intended to be equivalent and are used interchangeably.

The term "$C_1$-$C_4$ alkanol" refers to an alkane having from 1 to 4 carbon atoms wherein one or more hydrogens of the alkane are substituted with a hydroxyl group, typically with one hydroxyl group, i.e. the alkanols are typically mono-ols, e.g. ethanol. It is contemplated that the $C_1$-$C_4$ alkanol may include substitution wherein one or more hydrogen atoms of the alkane are each independently substituted with one or more groups selected from amino (including primary, secondary and tertiary amino), C=O, and halo (e.g. F, Cl). Typically, the $C_1$-$C_4$ alkanol is not substituted, e.g. ethanol.

The term $C_3$-$C_5$ ketone refers to an alkane having from 1 to 3 carbon atoms, wherein at least one non-terminal carbon is a carbonyl (i.e. C=O). Typically, only one such carbonyl group is present, i.e. the ketone is typically a monoketone, e.g. acetone. It is contemplated that the $C_3$-$C_5$ ketones may include substitution wherein one or more hydrogen atoms of the alkane backbone are each independently substituted with one or more groups selected from amino (including primary, secondary and tertiary amino), OH, and halo (e.g. F, Cl). Typically, the ketones are not substituted, e.g. acetone.

For avoidance of doubt, references herein to wt % amounts of components described on a "dry weight basis" are intended to refer to the quantity of the given component in the material relative to the total solids content of the material as a whole, i.e. is intended to exclude the mass of solvents such as water.

Herein, the term "gsm" means $g/m^2$. These two terms are used interchangeably.

DETAILED DESCRIPTION

According to the first aspect of the present invention, there is provided a method of manufacturing carboxymethylcellulose (CMC) fibres containing an antimicrobial, the fibres being suitable for use in the preparation of wound dressings, wherein the antimicrobial is selected from the group consisting of a biguanide, a biguanide derivative, octenidine, taurolidine, and a combination of two or more thereof, the method comprising:

submerging CMC fibres comprising at least 95 wt % carboxymethylcellulose in a treatment solution, the treatment solution comprising:

a) the antimicrobial, optionally in an amount of from 1-10 wt %; and b) at least 70 wt % of a water-miscible organic solvent selected from $C_1$-$C_4$ alkanols, $C_3$-$C_5$ ketones, and a combination of two or more thereof;

for a duration adequate to provide the CMC fibres containing the antimicrobial.

Within the context of the present invention, submerging means to cause at least some length of the CMC fibres, and preferably the entire length of the CMC fibres to be surrounded by the treatment solution around the entire fibre circumference. This term is intended to encompass "soaking", "dipping" or "wetting" of the CMC fibres into, or with, the treatment solution. In a typical embodiment, the fibres are submerged in a bath containing the treatment solution. The fibres being submerged may typically be continuous filament fibres. This method step may in principle be performed by pulling continuous filament fibres (e.g. in the form of a fibrous "tow") continuously through a treatment bath, such as where only part of the fibre length at any one time is submerged in the treatment solution, but wherein substantially all, or all of the fibre length is caused to be submerged in the treatment solution. The method is however preferably performed as a batch method by submerging entire fibre lengths (e.g. wherein the fibres are provided in the form of a tow) into a bath containing the treatment solution for an adequate duration. This has the advantage of evenly exposing the length of CMC fibres to the anti-microbial within the solution, which may thus in embodiments provide a generally even distribution of anti-microbial within the polymer. In such an embodiment, it will be appreciated that it may be advantageous to secure (e.g. by tying) the ends of the fibres/tow to maintain the integrity of the fibres/tow. Without wishing to be bound by theory, it is also believed that submerging the fibres in the treatment solution causes the fibre matrix to swell to permit penetration of the anti-microbial into the CMC fibre polymer matrix, providing effective loading of the anti-microbial into the polymer.

The CMC fibres being submerged in the treatment solution, in accordance with the first aspect of the present invention comprise at least 95 wt % CMC on a dry weight basis. In some embodiments, the CMC fibres comprise at least 96 wt %, 97 wt %, or 98 wt % CMC, optionally at least 99 wt % on a dry weight basis. In some embodiments, the CMC fibres that are submerged comprise 100% CMC on a dry weight basis. Preferably, the CMC fibres are entirely absent of any other fibre polymers. Preferably the CMC fibres are absent of alginates.

In embodiments, the CMC fibres submerged in the treatment solution are continuous fibres, also referred to in the art as continuous-filament fibres. Those skilled in the art will understand that continuous-filament fibres are long, continuous strands of fibres, which may be cut to a desired length. For example, CMC continuous-filament may be provided in lengths of from 1-250 m. The upper end of this scale is indicative of large-scale manufacturing facilities capable of processing extremely long fibres/tows, for instance using large vessels. In some embodiments, the fibres are provided (e.g. cut) to a length of 2-7 metres (m), optionally 3-6 m, optionally 4-5 m. In accordance with the method of the present invention, the CMC fibres may be a length (e.g. cut length) of CMC continuous-filament secured at each end of the length to retain the structural integrity the CMC continuous-filament. Securing may include tying-off the ends of the length of CMC continuous-filament/CMC fibres. In embodiments of the present invention, more than one CMC continuous-filament length is provided and submerged in the treatment solution. The CMC fibres may thus be provided as a continuous-filament, e.g. in the form of a tow of CMC fibres. The skilled artisan will appreciate that a "tow" refers to a longitudinally-parallel grouping of many continuous filament fibres, sometimes thousands of fibres, which can be conveniently transported through fibre treatment processes, e.g. using pulleys and spindles.

In embodiments, the antimicrobial is dissolved in the treatment solution e.g. entirely dissolved. Advantageously, this allows a homogeneous distribution of the antimicrobial to be provided within the treatment solution, and thereby allows uniform application of antimicrobial to the submerged CMC fibres.

It has been surprisingly found that submerging the CMC fibres with a treatment solution containing the anti-microbial in a solvent having the high organic content as claimed is able to incorporate the anti-microbial into the fibres at adequate levels to provide suitable elution and antimicrobial properties, but with improved softness and flexibility relative to prior art methods which use aqueous treatment solutions. This is exemplified in the examples herein by comparison to a comparative product produced by method whereby an aqueous solution of PHMB is sprayed onto a CMC wound dressing.

In some embodiments, the antimicrobial is selected from the group consisting of a biguanide, octenidine, taurolidine, and a combination of two or more thereof. In some embodiments, the antimicrobial is a biguanide. Exemplary biguanides for use in the invention include polyaminopropyl biguanide (PAPB), polyhexamethylene biguanide (PHMB), metmorfin (dimethylbiguanide), phenformin (phenethylbiguanide), propylbiguanide, buformin (butylbiguanide), hexylbiguanide, alexidine and chlorhexidine, with PHMB being particularly preferred. In some embodiments, the antimicrobial is PHMB, wherein the PHMB polymer backbone has between 2 and 30 repeating units. Advantageously, PHMB has been shown to have efficacy against a wide range of gram-positive and gram-negative microbes, and therefore is an excellent antimicrobial within the field of wound dressings, not least because open wounds may harbour a plethora of microbial species. PHMB has, for example, been shown to be effective against *Pseudomonas aeruginosa, Staphylococcus aureus* (also the methicillin-resistant type, MRSA), *Escherichia coli, Candida albicans* (yeast), *Aspergillus brasiliensis* (mold), vancomycin-resistant enterococci, and *Klebsiella pneumoniae* (implicated in pneumonia and bronchitis).

In embodiments, the treatment solution may comprise from 1-10 wt % of the antimicrobial, optionally 2-8 wt %, or 3-6 wt % antimicrobial, and further optionally 4-5 wt %. It has been found that the aforementioned concentrations of antimicrobial within the treatment solution provide suitable concentrations of antimicrobial in the CMC fibres containing the antimicrobial.

It may be appreciated that for some anti-microbial compounds, a degree of water may be required in the treatment solution to assist with solubility of the anti-microbial in the treatment solution. The treatment solution may comprise water in an amount of from 5-25 wt %, optionally 12-20 wt %, further optionally 15-18 wt %. Advantageously, it has been found that providing a high wt % of organic solvent, optionally in combination with a moderate (5-25 wt %) amount of water, has been found to effectively deliver the antimicrobial into the polymer matrix, and moreover, to prevent gelling of the CMC fibres. For example, in embodiments where the antimicrobial is PHMB, PHMB is highly water soluble but poorly soluble in organic solvents. It has been found that providing a treatment solution of PHMB in a treatment solution comprising water and a water-miscible organic solvent effectively delivers PHMB into the polymer network, yet advantageously does not result in gelling of the CMC fibres, unlike with methods wherein aqueous solutions are used to treat the CMC fibres, such as by spraying.

In some embodiments, the treatment solution comprises the water-miscible organic solvent in an amount of from 70-85 wt %, optionally 75-80 wt %, further optionally 76-78 wt %.

The water-miscible organic solvent may be selected from $C_1$-$C_4$ alkanols, such as 01-2 alkanols (e.g. ethanol). It may alternatively be a $C_3$-$C_5$ ketone (e.g. acetone). Combinations of two or more thereof are also contemplated. In some embodiments, the water-miscible organic solvent is selected from one or more of methanol, ethanol, propanol, isopropanol, and acetone. In preferred embodiments, the water-miscible organic solvent comprises, or consists of ethanol.

For instance, in some embodiments the water-miscible organic solvent comprises greater than 90 wt % ethanol, optionally greater than 95 wt % ethanol, optionally greater than 97 wt % ethanol. Advantageously, it has been found that ethanol provides CMC fibres containing the antimicrobial that have particularly enhanced and desirable softness and flexibility properties, as compared to other water-miscible solvents in accordance with the present invention.

In some embodiments, the water-miscible organic solvent is acetone. In some embodiments, the water-miscible organic solvent is ethanol and acetone, optionally wherein the ratio of ethanol to acetone is from 1:1 and 20:1. In some embodiments, the water-miscible organic solvent is ethanol and isopropanol, optionally wherein the ratio of ethanol to isopropanol is from 1:1 and 20:1.

In some embodiments, the antimicrobial-containing treatment solution may further comprise a pH adjustment agent, optionally an acid. In embodiments, the pH adjustment agent provides a pH of from 4.5 to 8.0 in the treatment solution after the CMC fibres have been submerged in the treatment solution. In some embodiments, the treatment solution comprises 0.1-0.9 wt % hydrochloric acid, optionally 0.4-0.6 wt % hydrochloric acid. Advantageously, the treatment solution comprising acid may ensure the final pH of the treatment solution, and therefore the pH of the CMC fibres produced following the treatment step is from 4.5 to 8.0.

In embodiments, the treatment solution may further comprise a metal-ion complexing agent, such as ethylenediaminetetetraacetic acid (EDTA), tetraxetan (DOTA), diethylenetriaminepentaacetic acid (DTPA), and the like. In some embodiments, the metal-ion complexing agent is EDTA. The treatment solution may comprise from 0.1-0.8 wt % metal-ion complexing agent, optionally 0.2-0.7 wt %, optionally still 0.3-0.6 wt %, further optionally 0.4-0.5 wt %. Advantageously, it has been surprisingly found that adding a metal-ion complexing agent, such as EDTA, to the treatment solution increases the availability of the antimicrobial to penetrate into the fibre polymer matrix. Metal-ion complexing agents, such as EDTA, are known to exhibit anti-biofilm properties and therefore are desirable agents for addition to CMC fibres for wound dressings.

In particularly advantageous embodiments, the anti-microbial treatment process as claimed can be performed as an additional step following the initial preparation of CMC fibres by carboxymethylation of a cellulose starting material. In embodiments, the CMC fibres submerged in the treatment solution according to the methods of the invention may therefore be formed by a process comprising reacting cellulose fibres with a carboxymethylating agent to provide the CMC fibres. In preferred embodiments, the cellulose fibres are provided as continuous-filament cellulose. The cellulose fibres may be natural or synthetic. The cellulose fibres may be derived from wood pulp (e.g. Eucalyptus, Oak, Birch wood). It is known for instance to use such wood pulp materials in a process where they are chemically broken down, and reformed into fibres. Suitable cellulose fibres for use as starting material for forming carboxymethylcellulose include rayon, e.g. viscose, e.g. Lyocell fibres. Optionally, the CMC fibres so formed may be subject to one or more washes to provide the CMC fibres containing at least 95 wt % CMC by dry mass weight to be submerged in the anti-microbial treatment solution of the present invention, e.g. to remove undesirable reaction products or surplus reagents.

Advantageously, it has been found that by preparing CMC fibres in situ from cellulose fibres, and then treating the resulting CMC fibres with the treatment solution comprising the antimicrobial according to the present claims, CMC fibres of the invention having excellent softness and flexibility are provided whilst also providing an efficient manufacturing process. Advantageously, the treatment solution of the present method can provide a dual function by virtue of it being able to act as part of the work-up of CMC fibres following carboxymethylation of cellulose, and by providing an antimicrobial finish to the CMC fibres.

In some embodiments reacting the cellulose fibres with a carboxymethylating agent comprises contacting the cellulose fibres with a base and a carboxymethylating agent, and optionally wherein the carboxymethylating agent is a chloroacetic acid salt, e.g. a monochloroacetate, preferably sodium monochloroacetate. In typical embodiments, the base is sodium hydroxide.

The cellulose fibres may be contacted with the base and the carboxymethylating agent concurrently, or sequentially. In some embodiments, the carboxymethylating agent and base are provided in a carboxymethylating solution and the cellulose fibres are submerged in the carboxymethylating solution. The carboxymethylating solution comprises the carboxymethylating agent, and optionally the base. In some embodiments, the carboxymethylating solution comprises 2-8 wt % carboxymethylating agent (e.g. sodium monochloroacetate), optionally 3-7 wt %, optionally still 4-6 wt %, e.g. 5 wt %. In some embodiments, the carboxymethylating solution comprises 0.5-8 wt % base (e.g. sodium hydroxide), optionally 1-7 wt %, optionally still 2-4 wt %, e.g. 2.5 wt %. In some embodiments, the carboxymethylating solution further comprises greater than 70 wt % of a water-miscible organic solvent selected from $C_1$-$C_4$ alkanols, $C_3$-05 ketones, and a combination of two or more thereof. In some embodiments, the carboxymethylating solution comprises the water-miscible organic solvent in an amount of from 70-85 wt %, optionally 75-80 wt %, further optionally 76-78 wt %. Advantageously, it has been found that using a solvent of around 70-85 wt % water-miscible organic solvent prevents undesirable gelling of the CMC fibres during the manufacturing process. The water-miscible organic solvent may be selected from any of those listed herein in respect of the treatment solution. The water-miscible organic solvent may thus be selected from one or more of methanol, ethanol, propanol, isopropanol, and acetone. In some embodiments, the water-miscible organic solvent is ethanol. In some embodiments, the water-miscible organic solvent comprises greater than 90 wt % ethanol, optionally greater than 95 wt % ethanol, optionally greater than 97 wt % ethanol. In some embodiments the carboxymethylating solution further comprises water in an amount of from 5-20 wt %, optionally 7-18 wt %, optionally still 9-16 wt %, further optionally 11-14 wt % e.g. 12 wt %.

In embodiments, the step of reacting the cellulose fibres with a carboxymethylating agent comprises submerging the cellulose fibres in a carboxymethylating solution as described herein, for a duration of from 0.5 to 3.5 hours, optionally from 1 to 3 hours, optionally still from 1.5 to 2.5 hours, e.g. 2 hours. In some embodiments, the carboxymethylating solution is maintained at a temperature in a range of from 55 to 85° C., optionally 60 to 80° C., optionally still 65 to 75° C., and further optionally 68 to 73° C. In some embodiments, following the step of submerging the cellulose fibres in the carboxymethylating solution, the CMC fibres are allowed to cool to a temperature in the range of from 40 to 60° C., optionally from 45 to 55° C. over a time period of from 10-20 minutes, optionally from 14-16 minutes e.g. 15 minutes.

The step of submerging the CMC fibres in the treatment solution may be preceded by a step of washing the CMC fibres with a pre-treatment wash solution. For instance, in particularly preferred embodiments, the CMC fibres are produced via the CMC-fibre forming step described above and are subjected to a pre-treatment wash solution prior to subjecting the CMC-fibres to the anti-microbial treatment step. This has the advantage of allowing certain by-products of the forming step, or other undesirable compounds to be removed prior to the anti-microbial treatment step. Preferably, the pre-treatment wash solution comprises:

(i) greater than 70 wt % of a water-miscible organic solvent selected from $C_1$-$C_4$ alkanols, $C_3$-$C_5$ ketones, and a combination of two or more thereof; and optionally (ii) a pH adjustment agent, optionally an acid.

A particularly preferred method is therefore a method of manufacturing carboxymethylcellulose (CMC) fibres containing an antimicrobial, the fibres being suitable for use in the preparation of wound dressings, wherein the antimicrobial is selected from the group consisting of a biguanide, a biguanide derivative, octenidine, taurolidine, and a combination of two or more thereof, the method comprising:

a) forming CMC fibres by a process comprising reacting cellulose fibres with a carboxymethylating agent to provide the CMC fibres; and b) washing the formed CMC fibres with a pre-treatment wash solution, the pre-treatment wash solution comprising greater than 70 wt % of a water-miscible organic solvent selected from $C_1$-$C_4$ alkanols, $C_3$-$C_5$ ketones, and a combination of two or more thereof; and optionally a pH adjustment agent, such as an acid, to provide pre-treated CMC fibres comprising at least 97 wt % carboxymethylcellulose on a dry weight basis; and c) submerging the pre-treated CMC fibres in a treatment solution, the treatment solution comprising:

a. the antimicrobial; and b. at least 70 wt % of a water-miscible organic solvent selected from $C_1$-$C_4$ alkanols, $C_3$-$C_5$ ketones, and a combination of two or more thereof;

for a duration adequate to provide the CMC fibres containing an antimicrobial.

In some embodiments, the pre-treatment wash solution comprises a pH adjustment agent (e.g. acid), optionally wherein the pH adjustment agent provides a pH of from 4.5 to 8.0, when the CMC fibres are submerged in the pre-treatment wash solution. The pH adjustment agent may be a base, an acid, or a buffer. In some embodiments, the pH adjustment agent is an acid, e.g. HCl.

The optional pH adjustment agent allows the pH of the CMC fibres to be adjusted to a suitable range prior to exposure of the pre-treated CMC fibres to the anti-microbial agent during the treatment step. Usually the anti-microbial is a relatively expensive component and so it is preferred to ensure that the pH is suitable for the given anti-microbial. In the case of biguanides such as PHMB, it is advantageous to ensure a pH in the pre-treatment solution of 4.5 to 8.

In some embodiments, the pH adjustment agent is an acid, e.g. HCl. This is for instance a suitable pH adjustment agent in the case whereby the CMC fibres are formed via a method comprising reacting carboxymethylating agent with cellulose in the presence of base (whereby the acid may neutralise an excess base and ensure any residual salts are dissolved).

Washing the CMC fibres with the pre-treatment wash solution may be performed by any suitable wash method, and may typically include submerging the CMC fibres in the pre-treatment wash solution, e.g. in a bath containing the pre-treatment wash solution. In some embodiments, the CMC fibres are submerged in the pre-treatment wash solution. In some embodiments, the CMC fibres are washed with, optionally submerged in, the pre-treatment wash solution of a duration of from 15 to 35 minutes, optionally 20 to 30 minutes, optionally still from 22 to 27 minutes, e.g. 25 minutes.

Advantageously, the pre-treatment wash solution causes the polymer matrix within the CMC fibres to expand/swell, and may remove any undesirable contaminants on the CMC fibres. Without wishing to be bound by theory, it is thought that causing the polymer matrix to expand/swell improves the penetration of the antimicrobial in the treatment solution throughout the polymer matrix.

CMC fibres may comprise basic salts, which require neutralisation by acid. These basic salts may be residually present from the manufacturing process of CMC, which typically requires the use of strong bases such as sodium hydroxide. In embodiments of the first aspect of the present invention described above wherein CMC fibres are prepared in situ from cellulose fibres, the pre-treatment wash solution comprises acid, e.g. HCl to neutralise residual base from the carboxymethylation step.

In some embodiments the pre-treatment wash solution comprises hydrochloric acid, optionally 0.1-0.9 wt % hydrochloric acid, further optionally 0.4-0.6 wt % hydrochloric acid. Advantageously, the neutralisation products of hydrochloric acid with the base typically used in carboxymethylation of cellulose (sodium hydroxide) are sodium chloride and water, both of which do not adversely affect the patient nor the performance of wound dressings comprising the CMC fibres. Moreover, advantageously, because of the high content (greater than 70 wt %) of water-miscible organic solvent in the pre-treatment wash solution, neutralisation salts such as sodium chloride may precipitate out of the pre-treatment wash solution, and are therefore removed from the CMC fibres.

In embodiments, the pre-treatment wash solution may comprise water in an amount of from 5-25 wt %, optionally 12-20 wt %, further optionally 15-18 wt %. Advantageously, as described above in respect of the treatment solution, it has been found that providing a high wt % of organic solvent in combination with a moderate (5-25 wt %) amount of water has been found to prevent gelling of the CMC fibres whilst allowing removal of impurities.

In embodiments, the pre-treatment wash solution comprises the water-miscible organic solvent in an amount of from 70-85 wt %, optionally 75-80 wt %, further optionally 76-78 wt %. Advantageously, it has been found that around 70-85 wt % water-miscible organic solvent prevents undesirable gelling of the CMC fibres during the manufacturing process.

In some embodiments the treatment solution and/or the pre-treatment wash solution is maintained at a temperature within the range of from 20° C. to 50° C. during the submerging step.

In embodiments, the CMC fibres may be submerged in the treatment solution for a duration of from 15 to 35 minutes, optionally from 20 to 30 minutes, and optionally still from 22 to 27 minutes, e.g. 25 minutes.

The step of submerging the CMC fibres in treatment solution according to methods of the invention may be followed by washing the CMC fibres containing antimicrobial with a post-treatment wash solution, the post-treatment wash solution preferably comprising:

(i) at least 98 wt % of a water-miscible organic solvent selected from $C_1$-$C_4$ alkanols, $C_3$-$C_5$ ketones, and a combination of two or more thereof; and optionally (ii) a spin finish agent (which may be a surfactant), optionally from 0.1-2.0 wt % or 1-1.5 wt % spin finish agent (e.g. surfactant).

In some embodiments the post-treatment wash solution comprises water in an amount of from 0.01-1.9 wt %, optionally 0.1-1.5 wt %, further optionally 0.5-1 wt %. In some embodiments the pre-treatment wash solution comprises the water-miscible organic solvent in an amount of at least 99 wt %.

Advantageously, submerging the CMC fibres in a post-treatment wash solution comprising predominately (at least 98 wt %) water-miscible organic solvent draws water out of the polymer matrix in the CMC fibres, which assists in the drying of the CMC fibres as described below. Moreover, advantageously, particularly where the antimicrobial is water-soluble (e.g. PHMB) but not soluble in organic solvents (e.g. PHMB), the post-treatment wash solution being predominately water-miscible organic solvent avoids washing the antimicrobial out of the CMC fibres.

In preferred embodiments, the post-treatment wash solution may advantageously comprise a spin finish agent and or surfactant. The spin finish agent may be a surfactant. Examples include polysorbates, e.g. Polysorbate 20 (Tween).

In embodiments, the method may further comprise removing solvent from the CMC fibres containing the antimicrobial, wherein the removing includes performing one or more of air drying, mechanical pressing, centrifugation, oven drying and vacuum extraction. The solvent to be removed may be the water-miscible organic solvent from the treatment solution and/or the post-treatment wash solution, and/or water. In embodiments, the removing may include oven drying at a temperature of from 25 to 40° C. for a duration of from 10 to 20 hours, optionally 14 to 18 hours. This has the effect that solvent is removed from the CMC fibres such that only residual amounts of water and/or water-miscible organic solvent remain in the fibres. Advantageously, removal of water from the CMC fibres prevents any undesired gelling of the fibres occurring during periods of storage of the CMC fibres and/or wound dressings comprising the CMC fibres.

In a preferred embodiment of the first aspect of the present invention is provided a method of manufacturing carboxymethylcellulose (CMC) fibres containing polyhexamethylene biguanide (PHMB), the fibres being suitable for use in the preparation of wound dressings, the method comprising:

(i) forming CMC fibres by a process comprising reacting cellulose fibres with a carboxymethylating agent to provide carboxymethylcellulose (CMC) fibres comprising at least 95 wt % CMC by dry weight basis (e.g. at least 97 wt %); and (ii) submerging the CMC fibres in a pre-treatment wash solution comprising a. greater than 70 wt % of a water-miscible organic solvent selected from $C_1$-$C_4$ alkanols, $C_3$-$C_5$ ketones, and a combination of two or more thereof; and optionally b. and pH adjustment agent adequate to maintain a pH in the treatment solution of pH 4-8; and (iii) submerging the pre-treated CMC fibres in a treatment solution comprising:

a. from 1-10 wt % PHMB; and b. at least 70 wt % of a water-miscible organic solvent selected from $C_1$-$C_4$ alkanols, $C_3$-$C_5$ ketones, and a combination of two or more thereof; for a duration adequate to provide CMC fibres containing PHMB; and (iv) submerging the CMC fibres containing PHMB in a post-treatment wash solution comprising:

a. at least 98 wt % of a water-miscible organic solvent selected from $C_1$-$C_4$ alkanols, $C_3$-$C_5$ ketones, and a combination of two or more thereof; and b. a spin finish agent (which may be a surfactant), optionally from 0.1-2.0 wt % spin finish agent (which may be a surfactant); and (v) optionally removing solvent from the CMC fibres containing the antimicrobial.

In some embodiments of the above process, all of the optional features are present. In some embodiments, the CMC fibres comprise from 0.05 to 0.8 carboxymethyl groups per glucose unit, optionally from 0.5 to 0.75 carboxymethyl groups per glucose unit, as determined by potentiometric titration.

In some embodiments, the carboxymethylcellulose (CMC) fibres containing the antimicrobial contain the antimicrobial dispersed throughout the fibre. Advantageously, the method of submerging the CMC fibres in the treatment solution comprising the antimicrobial causes the polymer matrix to expand, and the antimicrobial is able to penetrate into the CMC fibres. Moreover, by submerging the CMC fibres in the treatment solution, a larger surface area of the CMC fibre is exposed to the antimicrobial, and as such, it is anticipated that a more even distribution of antimicrobial is provided throughout the CMC fibre as compared to prior art methods such as spraying antimicrobial solutions onto fibres.

In embodiments, the method further comprises forming a wound dressing, or an article suitable for use in a wound dressing, comprising the respective (CMC) fibres containing the antimicrobial. The present disclosure thus contemplates use of the (CMC) fibres containing the antimicrobial obtained by the methods herein (e.g. fibres as described according to any of aspects two to four) in a method of forming a wound dressing, or forming an article suitable for use in a wound dressing. The fibres may be used to form a woven or non-woven article/material, preferably non-woven. For instance, forming the article/material may comprise weaving the fibres. Forming the article/material may comprise subjecting the fibres to needling/carding, e.g. to form a felt. The materials/wound dressing may be as described in accordance with any of the fourth to seventh aspects and embodiments herein.

According to a second aspect of the present invention, there is provided a carboxymethylcellulose (CMC) fibre containing an antimicrobial for use in the preparation of wound dressings, the CMC fibre obtained or obtainable by a method according to the first aspect of the present invention or any embodiments thereof. The definition of the antimicrobial presented in the first aspect and embodiments may therefore apply to this aspect.

According to a third aspect of the present invention, there is provided a carboxymethylcellulose (CMC) fibre containing an antimicrobial selected from a biguanide, a biguanide derivative, octenidine, taurolidine, and a combination of two or more thereof for use in the preparation of wound dressings wherein the antimicrobial is dispersed throughout the fibre polymer. In desirable embodiments, the anti-microbial is present throughout the body of the fibre and not simply at the surface. It is believed that this can be afforded by methods of the invention by virtue of the fibre polymer swelling in the treatment solution to allow ingress of the anti-microbial.

A fourth aspect provides a carboxymethylcellulose (CMC) fibre containing an antimicrobial selected from a biguanide, a biguanide derivative, octenidine, taurolidine, and a combination of two or more thereof for use in the preparation of wound dressings, wherein the CMC fibre polymer has not undergone gelation.

It is intended that the CMC fibres comprising antimicrobial according to the present invention may comprise additional additives, such as additives known to be useful in wound dressing applications. Such additives may include surfactants, spin finish agents and/or anti-biofilm agents (such as chelating agents, e.g. EDTA/DTPA). The spin finish agent may be a surfactant. Suitable spin finish agents include polysorbate, e.g. polysorbate 20 (Tween). In embodiments, such additives are provided in a total amount of no more than 5 wt %, e.g. no more than 4 wt %, 3 wt %, 2 wt % or 1 wt %. The CMC fibres of the invention may be absent of such additives.

The CMC fibres comprising antimicrobial according to the present invention (e.g. as defined in the second to fourth aspects herein) may comprise at least 95 wt % CMC relative to the total dry mass weight of the fibre, optionally at least 96 wt %, 97 wt %, 98 wt %, or optionally at least 99 wt %. Preferably, the CMC fibres are entirely absent of any other fibre polymers. Preferably the CMC fibres are absent of alginates.

According to a fifth aspect of the present invention, there is provided a woven, non-woven or knitted material comprising CMC fibres containing an antimicrobial, wherein the CMC fibres containing an antimicrobial are defined according to any one of the second, third or fourth aspects of the invention. The material is preferably a non-woven and most preferably a felt. The non-woven material may exhibit a conformability characterised by an overhang length of up to 6.5 cm, as determined by the Cantilever method described in ASTM D1388-08. Standardised methods for preparing the non-woven for testing by the Cantilever method are described herein in the general methods section (see conformability testing). The overhang length in the longitudinal direction may typically be from 4 to 6.5 cm, e.g. 4 to 6 cm. The overhang length in the longitudinal direction may in embodiments be no more than 6.2 cm, e.g. no more than 6 cm. In embodiments, this value is no more than 5.8 cm, 5.5 cm, or 5.3 cm. Preferably, the value is no more than 5.5 cm, e.g. no more than 5.0 cm.

According to a sixth aspect of the present invention, there is provided a non-woven material (preferably a felt) comprising entangled CMC fibres containing an antimicrobial, wherein the antimicrobial is selected from a biguanide, a biguanide derivative, octenidine, taurolidine, and a combination of two or more thereof, wherein the non-woven material exhibits a conformability characterised by an overhang length of up to 6.5 cm, as determined by the Cantilever method described in ASTM D1388-08. Standardised methods for preparing the non-woven for testing by the Cantilever method are described herein in the general methods section (see conformability testing). The overhang length in the longitudinal direction may typically be from 4 to 6.5 cm, e.g. 4 to 6 cm. The overhang length in the longitudinal direction may in embodiments be no more than 6.2 cm, e.g. no more than 6 cm. In embodiments, this value is no more than 5.8 cm, 5.5 cm, or 5.3 cm. Preferably the overhang length in the longitudinal direction is no more than 5.5 cm, e.g. no more than 5.0 cm. Methods described herein advantageously allow production of CMC fibres containing an anti-microbial agent whilst avoiding premature gelation. This therefore ensures that the CMC fibres retain softness, enabling production of resulting wound dressings that contain anti-microbial agent, but which still exhibit desirable conformability, as demonstrated by the relatively low overhang lengths recited, as determined by the Cantilever method.

According to a seventh aspect of the invention, there is provided a wound dressing comprising CMC fibres containing an antimicrobial, wherein the CMC fibres containing an antimicrobial are defined according to any one of the second, third or fourth aspects of the invention. The wound dressing may for instance contain a material according to the fifth or sixth aspects of the invention and the material is preferably a felt. The wound dressing may contain the material as the sole layer of the wound dressing, or typically the wound dressing may be a multi-layer dressing wherein the material is present as a layer within the multi-layer dressing.

In the CMC fibres containing anti-microbials of the invention, or the materials or wound dressings comprising such materials as defined in any of the second to seventh aspects herein, the antimicrobial may be present in the fibre in an amount of from 0.3 to 1.1 wt %, optionally from 0.5 to 0.9 wt %. In the CMC fibres containing anti-microbials, or the materials or wound dressings comprising such materials as defined in any of the second to seventh aspects herein, the antimicrobial may be selected from the group consisting of a biguanide, octenidine, taurolidine, and a combination of two or more thereof. In some embodiments, the antimicrobial is a biguanide. Exemplary biguanides for use in the invention include polyaminopropyl biguanide (PAPB), polyhexamethylene biguanide (PHMB), metmorfin (dimethylbiguanide), phenformin (phenethylbiguanide), propylbiguanide, buformin (butylbiguanide), hexylbiguanide, alexidine and chlorhexidine, with PHMB being particularly preferred. In some embodiments, the antimicrobial is PHMB, wherein the PHMB polymer backbone has between 2 and 30 repeating units. In any embodiments, the antimicrobial may be dispersed throughout the CMC fibre. In any embodiments, the carboxymethylcellulose (CMC) fibre containing an antimicrobial has desirably not undergone gelation.

Wound dressings in accordance with the seventh aspect of the present invention may be a multi-layer wound dressing comprising a non-woven fabric layer prepared using CMC fibres containing an antimicrobial according to the present invention, and one or more additional layers. The non-woven fabric layer may comprise greater than 98 wt % CMC fibres containing an antimicrobial according to the present invention, optionally greater than 99 wt %. The non-woven fabric layer may be a wound-contacting surface, or may be embedded between other layers in the multi-layer wound dressing. The multi-layer wound dressing may comprise a perforated wound-contacting layer, for example a perforated wound-contacting layer comprising polyurethane, which allows passage of exudate from the wound to the non-woven fabric layer. In some embodiments, the perforated wound-contacting layer further comprises an adhesive to adhere to the patient's skin. In some embodiments, the multi-layer wound dressings further comprise a semi-permeable layer, a film backing layer (e.g. polyurethane), a hydrocolloid and/or a foam-based layer. Advantageously, semi-permeable layers may assist in generating a moist environment for wounds to heal. In some embodiments, the non-woven fabric layer is between a perforated wound-contacting layer and a semi-permeable layer. Advantageously, this arrangement may increase absorbance of exudate from the wound, and/or improve fluid retention properties within the wound dressing.

A preferred wound dressing of the invention may comprise reinforced non-woven felt comprising a non-woven layer containing between 120-185 gsm of CMC fibres containing PHMB, the CMC fibres containing PHMB being needle bonded to a reinforcement layer of nominally 15-55 gsm made of nylon 6.6. Alternatively, reinforcing layers materials other than nylon 6.6 may be used, such as cellulose, polypropylene, polyester, PET, etc.

In some embodiments, the wound dressings may be a single layer wound dressing comprising a non-woven fabric layer prepared using CMC fibres containing an antimicrobial according to the present invention. The non-woven fabric layer may comprise greater than 95 wt %, e.g. at least 96 wt %, 97 wt %, 98 wt % or at least 99 wt % CMC fibres containing an antimicrobial according to the present invention, optionally greater than 99 wt %. In such embodiments, the wound dressing may be used in conjunction with a secondary wound dressing, wherein the secondary wound dressing includes a semi-permeable layer.

This disclosure also provides use of a) the fibres according to any of the second to fourth aspects and embodiments thereof described herein, or b) the material according to the fifth or sixth aspects or embodiments thereof described herein, or c) the wound dressing according to the seventh aspect or embodiments thereof described herein, in wound care, e.g. wound healing, or in a method of treating a wound. This application also provides a method of wound care, e.g. wound healing, or treating a wound, comprising applying the wound dressing according to the seventh aspect of the invention or any embodiment thereof to the wound. Also provided are CMC fibres containing an antimicrobial according to the second, third or fourth aspect or any embodiment thereof, for use in a method of treating a wound, or in wound care, e.g. wound healing, wherein the fibres are provided in a wound dressing according to the seventh aspect or any embodiment thereof, and the method comprises applying the wound dressing to the wound. Also provided is the use of CMC fibres containing an antimicrobial according to the second, third or fourth aspect or any embodiment thereof, in the manufacture of a wound dressing for treating a wound, or for wound care, e.g. for wound healing, wherein the treating comprises applying the wound dressing to the wound. The antimicrobial may be as described according to any embodiment herein, and is preferably PHMB. The antimicrobial may be as described according to any embodiment herein, and is preferably PHMB.

EXAMPLES

The following examples provide test methods and describe embodiments of the methods and products of the invention. The examples are intended to exemplify the invention but are not intended to be limiting on the scope of protection.

General Methods

Cantilever Test—Conformability Assay

The conformability of a non-woven fabric consisting of CMC fibres containing PHMB that were prepared according to the method of the present invention were investigated and comparative to the conformability of a comparative dressing not prepared according to the invention. This is described in example 5.

Several methods are known in the art for assessing the conformability and stiffness of fabrics, such as the cantilever test and the heart loop test. The data disclosed herein was obtained using the cantilever test as outlined below, and was in accordance with the cantilever method as approved by the American Society for Testing and Materials (ASTM) International (Designation D1388-08). The cantilever test employs the principle of cantilever bending of the fabric under its own weight.

A cantilever bending test apparatus ("Shirley Stiffness tester") having a horizontal surface was used for the conformability assay. Such apparatus are commercially available and described in detail in section 6 entitled "apparatus" in ASTM D1388-08, which is incorporated herein by reference. In accordance with the conformability Cantilever test described herein, the non-woven fabric for testing was prepared by the following method.

The CMC fibres to be tested (which may include antimicrobial in accordance with the invention) are opened and carded to form a non-woven structure comprising a nominal fibre weight between 125-185 GSM and needle-bonding density of 60-120 punches per square centimetre. The resulting non-woven felt is slit and cut to the required size to form a non-woven dressing ready for subjecting to the Cantilever method described below.

Samples of non-woven fibrous dressing as prepared by the method above and cut to a size of 25 mm×150 mm were slid along the horizontal surface at a rate of around 120 mm/min (+/−5%) in a direction parallel to a notional 'long dimension' of the sample. The sample was slid along the horizontal surface so that a leading edge projected from an edge of the horizontal surface. Sliding of the sample continued until the leading edge of the sample was depressed under the influence of gravity to the point where the angle formed between the leading edge and the horizontal surface was 41.5°. In other words, the weight of the overhang length of the sample causes the overhang length to depress under its own weight to an angle of 41.5° relative to the horizontal surface. The length of the resulting overhang was measured (in cm). From the measured lengths, the bending length was calculated, as described below under Example 5.

Owing to the non-directional orientation of fibres within non-woven fabrics, the method was repeated for each sample wherein the sample was rotated by 90° C. about its central axis perpendicular to the horizontal surface. In other words, the sample was rotated such that the sample was slid along the horizontal surface in a direction parallel to a notional 'short' dimension of the sample.

Example 1—Preparation of CMC Fibres Containing PHMB from Cellulose Fibres

A cellulose continuous filament (1.25 kg) of cellulose fibres was submerged in a carboxymethylating solution comprising 2.5 wt % sodium hydroxide, 13.5 wt % purified water (1.66 kg), 5 wt % sodium chloroacetate and 78 wt % ethanol. The resulting suspension was maintained at a temperature in the range of from 65 to 75° C., typically about 70° C., for a duration of around 2 hours.

The carboxymethylated cellulose continuous filament and carboxymethylating solution was allowed to cool to a temperature in the range of from 45° C. to 55° C., typically to about 50° C. and the resulting carboxymethylated cellulose continuous filament was then washed with a pre-treatment wash solution comprising 78 wt % ethanol, 21.5 wt % distilled water and 0.5 wt % hydrochloric acid to remove unreacted salts remaining from the carboxymethylation step and neutralise excess base. The wash was performed for around 25 minutes, at a temperature in the range of from 20° C. to 50° C., typically about 45° C. The pH of the wash solution after 20 to 30 minutes was between 4.5 and 8.0. The washed carboxymethylated cellulose continuous filament was then removed from the wash solution and subject to a treatment solution contain anti-microbial (PHMB). Other anti-microbials described herein may alternatively be provided.

The carboxymethylated cellulose continuous filament was submerged in a PHMB treatment solution comprising 4 wt % PHMB, 77 wt % ethanol, 0.4 wt % EDTA, 0.5 wt % hydrochloric acid, and 17 wt % purified water for 20 to 30 minutes at a temperature in the range of from 20° C. to 50° C., typically about 45° C., thus providing carboxymethylated cellulose continuous filament comprising PHMB. The carboxymethylated cellulose continuous filament comprising PHMB was then removed from the PHMB treatment solution. Other components suitable for wound dressing applications may also optionally be included in the treatment solution, such as anti-biofilm agents, or surfactants.

The carboxymethylated cellulose continuous filament comprising PHMB was then submerged in a final post-treatment wash solution comprising 99 wt % ethanol and 1 wt % polysorbate 20 (Tween) to remove excess water or other surplus materials, and provide desirable soft feel of the fibres, at a temperature in the range of from 20° C. to 50° C., typically around 45° C., for a duration of from 20 to 30 minutes. This post-treatment wash step may optionally be repeated if desired.

The carboxymethylated cellulose continuous filament comprising PHMB was then removed from the final wash solution, and dried by means of vacuum at a temperature of 40° C. to provide the dried carboxymethylated cellulose continuous filament comprising PHMB. The fibres were determined to contain 0.6% wt PHMB relative to the total weight of the fibres.

Example 2—Preparation of Non-Woven Felt Fabric

Those skilled in the art will be familiar with methods for preparing non-woven fabrics from fibres. An exemplary method is described below.

Continuous filaments of CMC fibres containing PHMB, prepared in accordance with Example 1, were cut into sections approximately 50 mm (2") in length. The sections of CMC fibres were separated from clumps of fibres into individual fibres using a coarse combing action. This stage may be referred to as 'fibre opening'. Following fibre opening, the CMC fibres were subjected to a finer combing action to separate all the fibres into individual fibres and to create a coherent, lightweight web, typically in the 10-20 g/m$^2$ range. The fibres in the web were orientated in the machine direction of the produced web. This stage may be referred to as 'carding'. Following carding, the web of CMC fibres was crosslapped with another layer of carded web. This process was continued until a density of nominally 150 g/m$^2$ was achieved was achieved. Each web layer was overlaid at 90° (in the cross direction) to the preceding web layer. This stage may be referred to as "crosslapping". Following crosslapping, a plurality of barbed needles were punched into the layered web produced during carding and removed therefrom multiple times. CMC fibres from the surface web layer were thereby drawn into other layers of the layered web structure, thereby entangling the fibres to create the felt. Of course, fibres in other web layers were also drawn into other layers.

Those skilled in the art will understand that the quantity and type of needles, the speed of needling and the penetration depth effect the properties of the resulting felt fabric. In the present examples, the process applied a 9 mm needle penetration depth at a needle board speed of 220 RPM. The needling action can be carried out in more than stage, and may be performed from one or both sides of the fibres.

Example 3—Preparation of Wound Dressing

Anti-microbial materials according to the invention, such as non-wovens as described above, may be incorporated into wound dressings in conventional ways. For instance, the anti-microbial material may be provided with a suitable backing layer and/or a skin contact layer, which may, in embodiments, be windowed. The backing layer and/or wound contact layer may be provided with an adhesive to assist the fixing of the wound dressing to the wound, such as a low trauma adhesive, e.g. a silicone adhesive.

Example 4—Gelling Test for CMC Fibres Containing PHMB

Approximately 4 cm of continuous filament CMC fibres containing PHMB prepared in accordance with Example 1 were cut. The fibres were separated out ('fibre opening') and dipped in distilled water for a minimum of 10 seconds. The fibres were withdrawn from the water and gelling visually inspected, wherein gelling was observed and gelled fibres were observed to be transparent.

Example 5—Conformability and Flexibility Testing

A non-woven fabric (Sample A) comprising CMC fibres containing PHMB according to the present invention was prepared according to the method described in Example 2. A comparative non-woven fabric comprising CMC fibres without PHMB incorporated, prepared by subjecting conventional CMC fibres to the method of example 2, was then prepared and sprayed with an aqueous solution of PHMB (Sample B). Spraying was performed as follows: an aqueous 20% PHMB solution was sprayed such that 1 gram of stock solution was sprayed onto the non-woven and the resulting concentration, which was calculated to amount to 0.6% of PHMB on the finished dressing, for comparison with Sample A of the invention. The sprayed samples were left to dry for a minimum of 16 hours.

Once prepared, Sample A was cut into six samples of 25×150 mm for testing in accordance with the cantilever method outlined above. Similarly, Sample B was cut into six comparative sized samples for testing. Each sample was slid in two directions with respect to the fabric: along the 'long' dimension, and along the 'short' dimension, as explained above. The results for each sample are set out in the table below.

For each sample, the test was conducted with the sample initially notionally 'facing upwards' (i.e. surface not in contact with the horizontal surface) with a notional 'front edge' leading towards the edge of the horizontal surface. The test was repeated with the sample facing upwards with the other 'back edge' leading. The test was repeated with the sample facing downwards ('reverse face') with the front edge leading. Finally, the test was repeated with the sample facing downwards with the back edge leading.

Face FE: Face upwards, front edge leading; Face BE: Face upwards; back edge leading; Reverse FE: Reverse upwards; front edge leading; Reverse BE: Reverse upwards; back edge leading.

TABLE 1

| | Long Dimension | | | | | | | |
| | Sample A (cm) | | | | Sample B (cm) | | | |
| | Face FE | Face BE | Reverse FE | Reverse BE | Face FE | Face BE | Reverse FE | Reverse BE |
|---|---|---|---|---|---|---|---|---|
| 1 | 4.05 | 4.00 | 4.90 | 4.75 | 6.00 | 6.30 | 7.40 | 7.35 |
| 2 | 4.10 | 4.25 | 5.20 | 4.95 | 5.90 | 5.95 | 6.50 | 6.30 |
| 3 | 4.15 | 3.95 | 4.90 | 5.00 | 6.15 | 6.60 | 7.45 | 7.25 |
| 4 | 4.25 | 4.30 | 4.80 | 4.90 | 7.00 | 6.95 | 7.35 | 7.05 |
| 5 | 4.00 | 4.15 | 4.85 | 5.05 | 7.00 | 6.90 | 7.45 | 7.55 |
| 6 | 4.25 | 4.05 | 5.10 | 5.00 | 6.85 | 7.00 | 7.40 | 7.35 |
| Avg. | 4.13 | 4.12 | 4.96 | 4.94 | 6.48 | 6.62 | 7.26 | 7.14 |
| Std Dev | 0.10 | 0.14 | 0.16 | 0.11 | 0.52 | 0.42 | 0.37 | 0.44 |

TABLE 2

| | Short Dimension | | | | | | | |
| | Sample A (cm) | | | | Sample B (cm) | | | |
| | Face FE | Face BE | Reverse FE | Reverse BE | Face FE | Face BE | Reverse FE | Reverse BE |
|---|---|---|---|---|---|---|---|---|
| 1 | 4.60 | 4.65 | 4.80 | 4.70 | 5.45 | 5.25 | 5.20 | 5.20 |
| 2 | 4.40 | 4.35 | 4.70 | 4.65 | 4.80 | 4.65 | 5.00 | 5.05 |
| 3 | 4.50 | 4.40 | 4.55 | 4.65 | 5.35 | 5.55 | 5.65 | 5.50 |
| 4 | 4.55 | 4.55 | 4.65 | 4.60 | 4.85 | 4.65 | 4.75 | 4.80 |
| 5 | 4.65 | 4.60 | 4.50 | 4.60 | 4.85 | 4.80 | 4.70 | 4.60 |
| 6 | 4.35 | 4.45 | 4.60 | 4.65 | 4.95 | 4.90 | 4.95 | 4.80 |
| Average | 4.51 | 4.50 | 4.63 | 4.64 | 5.04 | 4.97 | 5.04 | 4.99 |
| Std Dev | 0.12 | 0.12 | 0.11 | 0.04 | 0.28 | 0.36 | 0.35 | 0.33 |

The total averages and standard deviation for the long dimension (Table 3) and the short dimension (Table 4) are shown below.

TABLE 3

| Long Direction | Sample A (cm) | Sample B (cm) |
|---|---|---|
| Total Average | 4.54 | 6.88 |
| Std Dev | 0.026 | 0.061 |

TABLE 4

| Short Direction | Sample A (cm) | Sample B (cm) |
|---|---|---|
| Total Average | 4.57 | 5.01 |
| Std Dev | 0.04 | 0.03 |

As can be seen from Tables 3 and 4, Sample A (according to the invention) demonstrated bending at shorter lengths compared to Sample B (comparative example not according to the invention prepared by spraying dressing with aqueous PHMB solution), indicative of greater conformability for the wound dressing containing fibres prepared by methods of the present invention compared to the comparative example. This difference was most pronounced for tests performed in the notional 'longitudinal' direction (4.54 cm) on average, as compared to Sample B, which revealed a much longer length for fabric folding (6.88 cm) on average. These data are clearly indicative of increased softness and flexibility of the CMC fibres prepared according to the present invention and the resulting wound dressings prepared using such fibres according to the present invention.

Example 6—Antimicrobial Elution

A non-woven fabric prepared as described for Sample A under Example 5, and a comparative fabric not according to the invention, prepared in the manner described above for Sample B under Example 5, were tested to determine PHMB elution properties. The sample preparation and test method determination was conducted identically for both samples.

For each sample, a cut corresponding to 0.16 grams of the given non-woven fabric was gravimetrically measured. Each sample was placed in 100 g deionised water in a sample container and the sample lightly squeezed to ensure saturation with the water. The sample container was covered to prevent evaporation and left at ambient temperature for periods of 24 h, 48 h and 96 h (+/−30 min). After these respective periods, the PHMB concentration in the sample water, corresponding to eluted PHMB, was determined by photospectroscopic absorption using a Jenway 7305 UV-Vis Spectrometer, set to scan at 236 nm. This was performed by first running a blank control sample containing 3 mL deionised water in a 10 mm path-length quartz cuvette, followed by running a cuvette containing 3 mL of the given PHMB sample. A reading was obtained from the spectrometer for the sample, and the sample was rotated by 180 degrees before the reading was recorded again and the mean absorbency for the two readings calculated. This was performed for samples A and B at each of the above time frames, i.e. 24 h, 48 h and 96 h.

If the mean absorbance value is less than 0.592, the actual PHMB level can be obtained in ppm by multiplying the sample absorbance by 169. If the absorbance reading is greater than 0.592, the PHMB concentration is greater than 100 ppm and the solution should be diluted 10-fold until a suitable reading less than 0.592 is obtained, whereby the multiplication factor of 169 can be used, and the relevant dilution factored in. PHMB elution demonstrated by samples of the invention (referred to as Sample A) and the comparative samples (Sample B) are shown in table 5, whereby the values indicate the eluted concentration of PHMB in the solution in ppm at the defined time-periods.

TABLE 5

| Time period | Sample A (Invention) PHMB elution in ppm | Sample B (comparative) PHMB elution in ppm |
|---|---|---|
| 24 Hrs | 14.11 std dev: 0.848 | 13.25 std dev: 1.367 |
| 48 Hrs | 15.70 std dev: 2.093 | 15.04 std dev: 2.245 |
| 96 Hrs | 15.94 std dev: 1.6228 | 16.80 std dev: 3.2047 |

The data show that sample A of the invention desirably elutes PHMB and does so at a rate that is similar to the comparative example (Sample B).

Example 7—Antimicrobial Analysis

The Medicines & Healthcare Products Regulatory Agency (MHRA) and US Food and Drug Administration (FDA) require antimicrobial products, such as wound dressings prepared using the CMC fibres containing an antimicrobial in accordance with the present invention, to generate a 4 log reduction against a range of microorganisms. A 4 log reduction means the starting level of microorganisms is reduced by a factor of 10,000 ($10^4$), for example, typically starting levels in these tests would be $1×10^6$ colony forming units (CFU), these need to be reduced to at least $1 \times 10^2$ (100) or less. This translates into a 99.99% reduction of the inoculated bacterial population.

Test method AATCC100 "Antimicrobial Finishes on Textile Materials: Assessment of" is deemed as a suitable method to perform antimicrobial analysis. The AATCC-100 method was performed with the indicated microorganisms below and with samples of non-woven wound dressings prepared using the CMC fibres containing PHMB in accordance with the present invention. The log-fold reduction in bacteria are indicated in Table 6.

TABLE 6

| Microorganisms | Type | AATCC-100 |
|---|---|---|
| MRSA | Gram + | >6log |
| MRSE | Gram + | >6log |
| VRE | Gram + | >6log |
| Strep. Pyogenes | Gram + | >4log |
| Pseud. Aeruginosa | Gram – | >6log |
| E. Coli | Gram – | >6log |
| Kleb. Pneumoniae | Gram – | >5log |
| C. Albicans | Yeast | >6log |
| Rh. Mucilaginosa | Yeast | >6log |
| Trich. Mentagrophytes | Mould | >4log |
| Asp. Fumigatus | Mould | >5log |

As can be seen in Table 6, samples of wound dressings prepared using CMC fibres containing PHMB in accordance with the present invention were effective against a wide range of microorganisms including gram –ve and gram +ve bacteria, yeast, and moulds. Moreover, the log-fold reduction in bacterial growth for each microorganism tested was for all microbes tested at least 4, showing desirable efficacy in line with the requirements of the MHRA and FDA as outlined above.

--oOo-

In summary, from the data above, it is evident that the CMC fibres containing anti-microbial prepared according to the present invention provide desirable elution properties and an excellent anti-microbial effect in practice. The dressings provide these desirable functional properties whilst advantageously providing improved conformability compared to anti-microbial CMC wound dressings prepared according to prior art methods (e.g. whereby CMC dressings are sprayed with an aqueous solution of PHMB), thus providing improved wound dressings which would be more comfortable and effective for patients.

The methods of the invention can also be conveniently incorporated directly into the CMC-fibre forming process as described in detail above. This is possible without the need for additional drying or manipulation of the CMC fibre, but instead by taking the formed CMC-fibre material directly and applying a suitable wash regime, which may include submerging the CMC-fibre in an anti-microbial treatment solution as described in the first aspect of the invention.

--oOo-

Although the present invention has been described in detail, it should be understood that various changes, substitutions, and alterations are contemplated without departing from the principle and scope of the invention. Accordingly, the scope of the present invention should be determined by the following claims and their appropriate legal equivalents. The terms "a", "an" and "the" do not preclude the presence of multiple referents, unless the context clearly dictates otherwise. Optional or optionally means that the feature or activity may or may not be present. Either is contemplated. In embodiments, the optional feature or features may be present. Alternatively, the optional feature or features may not be present. Ranges may be expressed herein as from one particular value, and/or to another particular value, which is intended to be inclusive of the end-points of the range.

The invention claimed is:

1. A method of manufacturing carboxymethylcellulose (CMC) fibres containing an antimicrobial, the fibres being suitable for use in the preparation of wound dressings, wherein the antimicrobial is selected from the group consisting of a biguanide, a biguanide derivative, octenidine, taurolidine, and a combination of two or more thereof, the method comprising:
   submerging CMC fibres comprising at least 95 wt % carboxymethylcellulose on a dry weight basis in a treatment solution, the treatment solution comprising:
   a) the antimicrobial; and
   b) at least 70 wt % of a water-miscible organic solvent selected from $C_1$-$C_4$ alkanols, $C_3$-$C_5$ ketones, and a combination of two or more thereof;
   for a duration adequate to provide the CMC fibres containing an antimicrobial.

2. The method according to claim 1, wherein the CMC fibres submerged in the treatment solution are continuous filament fibres.

3. The method according to claim 1 wherein the antimicrobial is polyhexamethylene biguanide (PHMB).

4. The method according to claim 1, wherein the treatment solution comprises from 1-10 wt % of the antimicrobial agent relative to the total weight of the solution.

5. The method according to claim 1, wherein the treatment solution comprises water in an amount of from 5-25 wt % relative to the weight of the solution.

6. The method according to claim 1, wherein the treatment solution comprises the water-miscible organic solvent in an amount of from 70-85 wt % relative to the total weight of the solution.

7. The method according to claim 1, wherein the water-miscible organic solvent is selected from one or more of methanol, ethanol, propanol, isopropanol, and acetone.

8. The method according to claim 7, wherein the water-miscible organic solvent comprises at least 90 wt % ethanol relative to the total weight of the water-miscible organic solvent, optionally at least 95 wt % ethanol.

9. The method according to claim 1, wherein the step of submerging in CMC fibres in the treatment solution is preceded by a process of forming the CMC fibres, the process of forming the CMC fibres comprising:
   reacting cellulose fibres with a carboxymethylating agent to provide carboxymethylcellulose (CMC) fibres.

10. The method according to claim 1, wherein the step of submerging the CMC fibres in the treatment solution is preceded by a step of washing the CMC fibres with a pre-treatment wash solution.

11. The method according to claim 1, wherein the treatment solution is maintained at a temperature within the range of from 20° C. to 50° C. during the submerging step.

12. The method according to claim 1, wherein the CMC fibres are submerged in the treatment solution for a duration of from 15 to 35 minutes.

13. The method according to claim 1, wherein the step of submerging the CMC fibres is followed by washing the CMC fibres containing antimicrobial with a post-treatment wash solution, the post-treatment wash solution comprising:
   (i) at least 98 wt % of a water-miscible organic solvent selected from $C_1$-$C_4$ alkanols, $C_3$-$C_5$ ketones, and a combination of two or more thereof; and optionally (ii) a spin finish agent, optionally from 0.1-2.0 wt % spin finish agent.

14. The method according to claim 1, wherein the CMC fibres comprise from 0.05 to 0.8 carboxymethyl groups per glucose unit as determined by potentiometric titration.

15. A carboxymethylcellulose (CMC) fibre containing an antimicrobial within the polymer matrix of the carboxymethylcellulose fibre, wherein the antimicrobial is selected from a biguanide, a biguanide derivative, octenidine, taurolidine, and a combination of two or more thereof, for use in the preparation of wound dressings, wherein the antimicrobial is dispersed throughout the polymer matrix of the CMC fibre.

16. The CMC fibre containing an antimicrobial according to claim 15, wherein the antimicrobial is present in the fibre in an amount of from 0.3 to 1.1 wt %, relative to the total weight of the fibre.

17. The CMC fibre containing an antimicrobial according to claim 15, wherein the antimicrobial is polyhexamethylene biguanide (PHMB).

18. A woven, non-woven or knitted material comprising CMC fibres according to claim 15.

19. A non-woven material comprising entangled CMC fibres according to claim 15, wherein the non-woven material exhibits a conformability characterised by an overhang length of up to 6.5 cm in the long dimension, as determined by the Cantilever method described in ASTM D1388-08.

20. A wound dressing comprising CMC fibres according to claim 15.

* * * * *